(12) United States Patent
Cheung et al.

(10) Patent No.: US 6,184,195 B1
(45) Date of Patent: Feb. 6, 2001

(54) BLOOMING TYPE GERMICIDAL HARD SURFACE CLEANERS COMPRISING BIPHENYL-BASED SOLVENTS

(75) Inventors: Tak Wai Cheung, Bridgewater; Dennis Thomas Smialowicz, Waldwick; Minaxi Hemansu Mehta, Fairlawn; Ralph Edward Rypkema, Lodi, all of NJ (US)

(73) Assignee: Reckitt Benckiser Inc., Wayne, NJ (US)

( * ) Notice: Under 35 U.S.C. 154(b), the term of this patent shall be extended for 0 days.

(21) Appl. No.: 09/178,137

(22) Filed: Oct. 23, 1998

(30) Foreign Application Priority Data

Nov. 28, 1997 (GB) .................................................. 9725093

(51) Int. Cl.[7] ................ C11D 3/44; C11D 1/62
(52) U.S. Cl. .............. 510/432; 510/245; 510/342; 510/356; 510/382; 510/384; 510/391; 510/405; 510/432; 510/463; 510/504
(58) Field of Search ................... 510/382, 384, 510/391, 463, 504, 432, 356, 405, 245, 342

(56) References Cited

U.S. PATENT DOCUMENTS

| 5,591,708 | 1/1997 | Richter ................... 510/463 |
| 5,811,383 | * 9/1998 | Klier et al. ............... 510/417 |

FOREIGN PATENT DOCUMENTS

| 195 37 782 A1 | 4/1997 | (DE) ............... A01N/65/00 |
| 2 304 112 | 3/1997 | (GB) ............... C11D/3/48 |
| 2 306 500 | 5/1997 | (GB) ............... C11D/3/43 |
| WO96/06153 | 2/1996 | (WO) ............... C11D/3/00 |
| WO97/06230 | 2/1997 | (WO) ............... C11D/1/65 |

OTHER PUBLICATIONS

Copy of GB Search Report for GB Application No. 9725093.0 dated Feb. 27, 1998.
Copy of PCT International Search Report for PCT/US98/22783 dated Mar. 10, 1999.

* cited by examiner

*Primary Examiner*—Yogendra Gupta
*Assistant Examiner*—Charles Boyer
(74) *Attorney, Agent, or Firm*—Fish & Richardson P.C.

(57) ABSTRACT

An aqueous concentrated liquid disinfectant composition which blooms when added to a larger volume of water which comprises the following constituents:

a terpene based solvent;

germicidal cationic surfactant, preferably a quaternary ammonium compound having germicidal properties;

organic solvent constituent;

a binary co-solvent system comprising alkyl diphenyl solvent and a co-solvent;

one or more nonionic surfactants;

optionally but desirably at least one optional constituent selected from: chelating agents, coloring agent, light stabilizers, fragrances, thickening agents, hydrotropes, pH adjusting agents, pH buffers one or more detersive surfactant constituents particularly non-ionic and amphoteric surfactants, as well as others known the art and useful in similar compositions; and, the balance being water.

The liquid disinfectant compositions feature good blooming characteristics, particularly good long term blooming retention.

Process for the use of the compositions are also disclosed.

12 Claims, No Drawings

BLOOMING TYPE GERMICIDAL HARD SURFACE CLEANERS COMPRISING BIPHENYL-BASED SOLVENTS

The present invention relates to disinfectant compositions. More particularly the present invention relates to concentrated liquid disinfectant compositions which are normally diluted in a larger volume of water to form a working solution therefrom, and which exhibit a blooming effect when diluted.

Blooming is a property exhibited by dilutable compositions such as known cleaning compositions, specifically pine-oil type cleaning compositions which contain a significant amount (generally at least about 5% and more) of pine oil. Certain phenolic disinfectant compounds, such as LYSOL® disinfectant concentrate (Reckitt & Colman, Inc., Montvale, N.J.) also exhibit such a blooming property. Blooming may be characterized as the formation of milky, creamy or cloudy appearance which is manifested when a dilutable composition is added to a larger volume or quantity of water. Blooming is an important characteristic from a consumer standpoint as it provides a visual indicator and impression to the consumer that the concentrated product contains active cleaning and/or disinfecting constituents which are released upon addition of the concentrate to a volume of water. Such is an important visual indicator of apparent efficacy of a concentrated product.

While such pine oil type cleaning compositions are commercially significant and in popular use, their use is not without attendant shortcomings. For example, high levels of pine oil in a cleaning composition are known to leave undesirable surface residues, particularly on hard surfaces. This effect may be minimized by the addition of further constituents, such as the use of certain surfactants which are useful in solubilizing and stabilizing the pine oil. However, such a solution raises further problems as many useful surfactants, and frequently the pine oil itself, are categorized as undesired volatile organic compounds ("VOC"). Thus, there is need in the art for providing improved pine oil type cleaning compositions which exhibit one or more of the identifying characteristics outlined above which are important indicia for consumer acceptance, while at the same time providing a reduction in the content of undesired volatile organic compounds which are often used in commercially available pine oil type cleaning compositions.

While presently commercially available materials have advantageous features, they are not without their attendant shortcomings as well. For example, the use of pine oil, and its pungent characteristic odor is frequently not desired. Also, such compositions frequently are directed to providing a cleaning effect, and do not provide an appreciable sanitizing effect. Further, certain compositions known to the art may not provide a bloom which is long lasting, or which is not particularly substantive.

It has now been found that it is now possible to produce certain concentrate compositions utilizing these selected constituents in particular formulations which provide blooming type cleaning compositions in a concentrated liquid form which provide both a germicidal effect and a good blooming effect. The "blooming" observed may be described as the change of the water's appearance from essentially colorless and transparent to that of a milky white or milky yellowish white, cloudy appearance. This effect is also sometimes referred to as the "break". Such blooming is a highly desirable in blooming type cleaning compositions as consumer/end user expectations associate cleaning effectiveness with the extent and degree of this blooming upon formation of a cleaning composition. Such blooming is particularly desirable in compositions where the blooming characteristic in an aqueous dilution is particularly pronounced, or "substantive" and is long lasting in such aqueous dilutions.

According to one aspect of the invention, there is provided an aqueous concentrated liquid disinfectant composition which blooms when added to a larger volume of water which comprises the following constituents:
  a terpene based solvent;
  germicidal cationic surfactant, preferably a quaternary ammonium compound having germicidal properties;
  organic solvent constituent;
  a binary co-solvent system comprising alkyl biphenyl solvent and a co-solvent;
  one or more nonionic surfactants;
  optionally but desirably at least one optional constituent selected from: chelating agents, coloring agent, light stabilizers, fragrances, thickening agents, hydrotropes, pH adjusting agents, pH buffers one or more detersive surfactant constituents particularly non-ionic and amphoteric surfactants, as well as others known the art and useful in similar compositions; and,
  the balance being water.

The one or more optional constituents when present, and are included in amounts which do not undesirably affect the overall blooming characteristics of the present inventive compositions.

In preferred embodiments the terpene based solvent constituent is present with respect to the alkyl biphenyl solvent in a respective weight ratio of from 8:1 to 1:2, with the total amount of these combined constituents not exceeding 9% wt. of the total weight of the concentrate compositions.

In preferred embodiments the concentrate compositions provide excellent initial blooming characteristics in 'as mixed' dilutions with water, which are particularly substantive, and which also exhibit good retention of blooming characteristics over a longer time period, viz., days and weeks.

In a further aspect of the invention there is provided commercially acceptable shelf stable concentrated cleaning compositions which exhibit one or more of the identifying characteristics of pine oil type cleaning compositions described above, (particularly those which exhibit reduced amounts of VOC), which concentrated cleaning compositions are readily dilutable with water to form useful cleaning compositions.

According to a further aspect of the invention there is provided a concentrated liquid disinfectant composition wherein the composition exhibits a germicidal effect in both its concentrated form, and in an aqueous diluted form. Desirably, such a concentrated liquid disinfectant composition which in a diluted form provides disinfection of surfaces wherein the presence of gram positive type pathogenic bacteria such as *Staphylococcus aureus,* and/or the presence of gram negative type pathogenic bacteria such as *Salmonella choleraesuis* and/or *Pseudomonas aeruginosa* is suspected.

The terpene containing solvent constituent, includes one or more further terpene based solvents. These terpene containing solvents preferably include mono- and bicyclic monoterpenes, i.e., those of the hydrocarbon class, which include, for example, the terpinenes, terpinolenes, limonenes, pinenes and mixtures thereof. Useful terpenes include d-limonene, and the mixture of terpene hydrocarbons obtained from the essence of oranges, e.g., cold-pressed orange terpenes and orange terpene oil phase ex fruit juice, and the mixture of terpene hydrocarbons expressed from lemons and grapefruit. The foregoing terpene hydrocarbon solvents are include derivatives of citrus fruits and citrus fruit by-products and, therefore, are naturally occurring materials. Numerous other terpene hydrocarbons are known to those skilled in the art and may be used to prepare the blooming type, germicidal hard surface cleaning and disinfecting compositions of the present invention; however, those as mentioned above recited which are based on d-limonene and the mixture of terpene hydrocarbons obtained from citrus fruits are the most readily available and, hence, are preferred. Of these d-limonene is the most prefererred.

These terpene containing solvent constituents are typically supplied as technical grade materials which may be and are often formulated with small amounts, e.g., 0.1% wt. (weight percent,) of auxiliary materials such as one or more stabilizers, e.g., antioxidants such as butylated hydroxytoluene. Such auxiliary materials are included within the meaning of the term "terpene containing solvent", as employed in this specification and the accompanying claims. It is also to be understood that mixtures of two or more terpene containing solvents constituents may also be used to form the terpene containing solvent in the compositions according to the invention.

The concentrate compositions of the invention desirably comprise a terpene based constituent which may be a pine oil constituent, or a d-limonene constituent or which may include both these materials. Pine oil is an organic solvent, and is a complex blend of oils, alcohols, acids, esters, aldehydes and other organic compounds. These include terpenes which include a large number of related alcohols or ketones. Some important constituents include terpineol, which is one of three isomeric alcohols having the basic molecular formula $C_{10}H_{17}OH$. Useful pine oils include synthetic pine oil, and also include steam distilled and sulfate pine oils, and will generally contain a higher content of turpentine alcohols. Other important compounds include alpha- and beta-pinene (turpentine), abietic acid (rosin), and other isoprene derivatives.

Particularly effective pine oils which are presently commercially available include Glidco® Pine Oil 60 (believed to contain approximately 60% terpene alcohols), Glidco® Pine Oil 80 (believed to contain approximately 80% terpene alcohols) Glidco® Pine Oil 150 (believed to contain approximately 85% terpene alcohols); Glidco® Terpene SW (believed to contain approximately 75% terpene alcohols); as well as Glidco® Terpineol 350 (believed to contain approximately 100% terpene alcohols). Each of these may be obtained from available from Glidco Organics Corp., Jacksonville, Fla. (USA). Other products which can contain up to 100% pure alpha-terpineol, may also be used in the present invention.

Particularly useful d-limonene containing compositions which are useful in the terpene containing solvent constituent according to the invention include mixtures of terpene hydrocarbons obtained from the essence of oranges, e.g., cold-pressed orange terpenes and orange terpene oil phase ex fruit juice, and the mixture of terpene hydrocarbons expressed from lemons and grapefruit.

The terpene containing solvent constituent may be present in the concentrate compositions in amounts of from about 0.001% by weight to up to about 20% by weight, preferably about 0.1–15% by weight, most preferably in amount of between 1–12% by weight. When a pine oil constituent is present, preferred are pine oil preparations which comprise at least about 50% terpene alcohols, more desirably at least about 60% terpene alcohols.

According to certain preferred embodiments, the terpene solvent constituent is solely a d-limonene constituent.

According to certain preferred embodiments, the terpene solvent constituent is solely a pine oil constituent.

As with all of the weight percentages of the constituents described, the weight percentages are indicative of the weight percentages of the actives in a named constituent containing preparation.

The concentrate compositions according to the invention include as a necessary constituent at least one cationic surfactant which is found to provide a broad antibacterial or sanitizing function. Any cationic surfactant which satisfies these requirements may be used and are considered to be within the scope of the present invention, and mixtures of two or more cationic surface active agents, viz., cationic surfactants may also be used. Cationic surfactants are well known, and useful cationic surfactants may be one or more of those described for example in *McCutcheon's Detergents and Emulsifiers,* North American Edition, 1982; *Kirk-Othmer, Encyclopedia of Chemical Technology,* 3rd Ed., Vol. 22, pp. 346–387, the contents of which are herein incorporated by reference.

Examples of preferred cationic surfactant compositions useful in the practice of the instant invention are those which provide a germicidal effect to the concentrate compositions, and especially preferred are quaternary ammonium compounds and salts thereof, which may be characterized by the general structural formula:

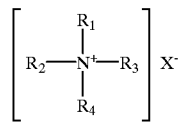

where at least one of $R_1$, $R_2$, $R_3$ and $R_4$ is a alkyl, aryl or alkylaryl substituent of from 6 to 26 carbon atoms, and the entire cation portion of the molecule has a molecular weight of at least 165. The alkyl substituents may be long-chain alkyl, long-chain alkoxyaryl, long-chain alkylaryl, halogen-substituted long-chain alkylaryl, long-chain alkylphenoxyalkyl, arylalkyl, etc. The remaining substituents on the nitrogen atoms other than the abovementioned alkyl substituents are hydrocarbons usually containing no more than 12 carbon atoms. The substituents $R_1$, $R_2$, $R_3$ and $R_4$ may be straight-chained or may be branched, but are preferably straight-chained, and may include one or more amide, ether or ester linkages. The counterion X may be any salt-forming anion which permits water solubility of the quaternary ammonium complex.

Exemplary quaternary ammonium salts within the above description include the alkyl ammonium halides such as cetyl trimethyl ammonium bromide, alkyl aryl ammonium halides such as octadecyl dimethyl benzyl ammonium bromide, N-alkyl pyridinium halides such as N-cetyl pyridinium bromide, and the like. Other suitable types of quaternary ammonium salts include those in which the molecule contains either amide, ether or ester linkages such as octyl phenoxy ethoxy ethyl dimethyl benzyl ammonium chloride, N-(lauryl cocoaminoformylmethyl)-pyridinium chloride, and the like. Other very effective types of quaternary ammonium compounds which are useful as germicides include those in which the hydrophobic radical is characterized by a substituted aromatic nucleus as in the case of lauryloxyphenyltrimethyl ammonium chloride, cetylaminophenyltrimethyl ammonium methosulfate, dodecylphenyltrimethyl ammonium methosulfate, dodecylbenzyltrimethyl ammonium chloride, chlorinated dodecylbenzyltrimethyl ammonium chloride, and the like.

Preferred quaternary ammonium compounds which act as germicides and which are be found useful in the practice of the present invention include those which have the structural formula:

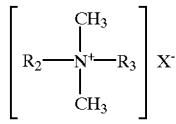

wherein $R_2$ and $R_3$ are the same or different $C_8$–$C_{12}$alkyl, or $R_2$ is $C_{12-16}$alkyl, $C_{8-18}$alkylethoxy, $C_{8-18}$alkylphenolethoxy and $R_3$ is benzyl, and X is a halide, for example chloride, bromide or iodide, or is a methosulfate anion. The alkyl groups recited in $R_2$ and $R_3$ may be straight-chained or branched, but are preferably substantially linear.

Particularly useful quaternary germicides include compositions which include a single quaternary compound, as well as mixtures of two or more different quaternary compounds. Particularly useful quaternary germicides include which are described as being a blend of alkyl dimethyl benzyl ammonium chlorides; BARDAC® 205M, BARDAC® 2050, BARDAC® 2080, BARDAC® 2250, BTC® 812, BTC® 818 and BTC® 1010 which are described as being based on dialkyl($C_8$–$C_{10}$)dimethyl ammonium chloride; BARDAC® 2250 and BARDAC® 2280 or BTC® 1010 which are described as being a composition which includes didecyl dimethyl ammonium chloride; BARDAC® LF and BARDAC® LF 80 which are described as being based on dioctyl dimethyl ammonium chloride; BARQUAT® MB-50, BARQUAT® MB-80, BARQUAT® MX-50, BARQUAT® MX-80, BARQUAT® OJ-50, BARQUAT® OJ-80, BARDAC® 208M, HYAMINE® 3500, HYAMINE® 3500-NF, BTC® 50, BTC® 824, BTC® 835, BTC® 885, BTC® 2565, BTC® 2658, BTC® 8248 or BTC® 8358 each described as being based on alkyl dimethyl benzyl ammonium chloride (benzalkonium chloride); BARQUAT® 4250, BARQUAT® 4280, BARQUAT® 4250Z, BARQUAT® 4280Z, BTC® 471, BTC® 2125, or BTC® 2125M each described as being a composition based on alkyldimethylbenzyl ammonium chloride and/or alkyldimethylethylbenzyl ammonium chloride; BARQUAT® MS-100 or BTC® 324-P-100 each described as being based on myristyldimethylbenzyl ammonium chloride; HYAMINE® 2389 described as being based on methyldodecylbenzyl ammonium chloride and/or methyldodecylxylene-bis-trimethyl ammonium chloride; HYAMINE® 1622 described as being an aqueous solution of benzethonium chloride; as well as BARQUAT® 1552 or BTC® 776 described as being based on alkyl dimethyl benzyl ammonium chloride and/or dialkyl methyl benzyl ammonium chloride, BARQUAT® 50-MAB described as being based on alkyldimethylethyl ammonium bromide and LONZABAC®-12.100 described as being based on an alkyl tertiary amine. Polymeric quaternary ammonium salts based on these monomeric structures are also considered desirable for the present invention. One example is POLYQUAT® described as being a 2-butenyldimethyl ammonium chloride polymer. (Each of these recited materials are presently commercially available from Lonza, Inc., Fairlawn, N.J. and/or from Stepan Co., Northfield, Ill.)

The germicidal cationic surfactant may be present in the concentrate compositions in amounts of from about 0.001% by weight to up to about 15% by weight, preferably about 0.1–10% by weight, most preferably in amount of between 1–5% by weight.

A further constituent according to the invention is an organic solvent which is present in addition to the pine oil which is itself known to be an organic solvent and assists in improves the dispersability and/or miscibility of the water insoluble pine oil in water. The organic solvent may also improve the miscibility of further constituents according to the present invention, including any water insoluble or poorly soluble constituents. Many useful organic solvent which are known to be useful in dispersing pine oil in water may be used; virtually any may be used as long as it does not undesirably disrupt the favorable characteristics of the invention, especially the blooming characteristic. Mixtures of two or more organic solvents may also be used as the organic solvent constituent.

Useful organic solvents are those which are at least partially water-miscible such as alcohols, water-miscible ethers (e.g. diethylene glycol diethylether, diethylene glycol dimethylether, propylent glycol dimethylether), water-miscible glycol ether (e.g. propylene glycol monomethylether, propylene glycol mono ethylether, propylene glycol monopropylether, propylene glycol monobutylether, ethylene glycol monobutylether, dipropylene glycol monomethylether, diethyleneglycol monobutylether), lower esters of monoalkylethers of ethyleneglycol or propylene glycol (e.g. propylene glycol monomethyl ether acetate) all commercially available from Union Carbide, Dow Chemicals or Hoescht. Mixtures of organic solvents can also be used.

Particularly useful organic surfactants include water soluble or water miscible alcohols including alkyl alcohols such as n-propanol and isopropanol, aromatic alcohols, as well as alkylaryl alcohols such as phenylmethanol.

Further useful organic solvents include glycols and glycol ethers. Examples of such glycol ethers include those having the general structure R'—O—R"—OH, wherein R' is an alkoxy of 1 to 20 carbon atoms, or aryloxy of at least 6 carbon atoms, and R" is an ether condensate of propylene glycol and/or ethylene glycol having from one to ten glycol monomer units. Examples of such useful glycol ethers include propylene glycol methyl ether, dipropylene glycol methyl ether, tripropylene glycol methyl ether, propylene glycol isobutyl ether, ethylene glycol methyl ether, ethylene glycol ethyl ether, ethylene glycol butyl ether, diethylene glycol phenyl ether, propylene glycol phenol ether, and mixtures thereof. Preferred are ethylene glycol n-butyl ether, diethylene glycol n-butyl ether, and mixtures thereof. Such glycol ethers are presently commercially available from a number of sources including in the DOWANOL™ glycol ether from The Dow Chemical Company, Midland Mich. (USA).

Further particularly useful organic solvents monohydric (straight chained or branched) primary, secondary or tertiary lower aliphatic alcohols, especially $C_1$–$C_6$ aliphatic primary and secondary alcohols, of which isopropanol is particularly preferred. It has been observed by the inventors that the inclusion of at least one $C_1$–$C_6$ aliphatic primary or secondary alcohols, and especially isopropanol, functions as a hydrotrope to maintain the stability and dissolution of other constituents in the present inventive compositions.

It has generally been found the addition of only a minimum effective amount which is found to be effective in dispersing or solubilizing the pine oil constituent and any other aqueous insoluble or poorly soluble constituents in the concentrate compositions is desirably used. Such is due to desire to reduce the amount of volatile organic constituents in the concentrate compositions of the invention, which volatile organic constituents are desirably minimized from an environmental standpoint. The present inventors have found that inclusion of the organic solvent constituent in amounts of about 0.001% by weight to about 20% by weight have been found to be effective to solubilize the pine oil, as well as in solubilizing other less water soluble constituents present in the concentrate compositions of the invention. Preferably, the organic solvent constituent is present in amounts of from 0.1–18% by weight, and most preferably from about 0.1–15% by weight.

The inventive compositions also include a binary co-solvent system comprising alkyl biphenyl solvent and a co-solvent which aids in the solubilization of the diphenyl solvent in an aqueous medium.

The alkyl biphenyl solvent is one which may be generally represented by the formula:

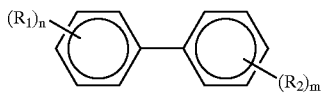

wherein:

$R_1$ is hydrogen or is a lower alkyl radical, preferably a $C_1$–$C_{10}$, but more preferably is a $C_1$–$C_6$ straight chained or branched alkyl radical, $R_2$ is a lower alkyl radical, preferably a $C_1$–$C_{10}$, but more preferably is a $C_1$–$C_6$ straight chained or branched alkyl radical, m is an integer from 1–3 inclusive; and, n is an integer from 1–3 inclusive.

Preferably $R_1$ is hydrogen, n is 1, and $R_2$ has any of the values indicated above. More preferably, $R_1$ is hydrogen and n is 1, and $R_2$ is a $C_1$–$C_6$ straight chained or branched alkyl radical. It is to be understood that mixtures of the compounds indicated above may be used as the biphenyl solvent constituent.

Such alkyl biphenyls are, per se, known to the art, and are described in U.S. Pat. No. 3,787,181. Particularly useful as the alkyl biphenyl solvent are materials presently marketed as NUSOLV ABP solvents (Ridge Technologies Inc., Ridgewood, N.J.) described to be a high purity alkyl biphenyls and mixtures thereof.

The alkyl biphenyl solvent may be present in the concentrate compositions in amounts of from about 0.001% by weight to up to about 20% by weight, preferably about 0.1–15% by weight, most preferably in amount of between 1–10% by weight.

Preferably when the concentrate composition includes a pine oil constituent as the sole terpene solvent constituent, the alkyl biphenyl solvent is desirably present in a respective weight ratio of pine oil constituent:alkyl biphenyl solvent of from 8:1 to 3:6, with further more preferred ratios being demonstrated by the Examples discussed below.

Preferably when the concentrate composition includes a d-limonene constituent as the sole terpene solvent constituent, the alkyl biphenyl solvent is desirably present in a respective weight ratio of d-limonene constituent:alkyl biphenyl solvent of from 4:3.5 to 5:2, and most preferably about 3:4, with further most preferred ratios being demonstrated by the Examples discussed below.

The inventors have observed that the concentrated compositions of the invention are greatly improved with the addition of a co-solvent. This co-solvent aids in the solubilization of the alkyl biphenyl solvent in water is desirably an at least partially water-miscible alcohol, especially aromatic and aliphatic alcohols. Particularly effective are aromatic alcohols, especially benzyl alcohols. The inventors have found that the inclusion of such alcohols greatly aids in the dissolution of the alkyl biphenyl solvents in the concentrate compositions according to the invention being described herein, which aids in ensuring that clarity of the concentrate composition is maintained which is particularly desirable from a consumer standpoint.

The co-solvent may be present in the concentrate compositions in amounts of from about 0.001% by weight to up to about 10% by weight, preferably about 0.1–5% by weight, most preferably in amount of between 0.1–2% by weight.

Alternately, it is contemplated that the preferred co-solvent described above may be substituted in whole or in part by one or more nonionic or amphoteric surfactants which are also shown to aid in the dissolution of the alkyl biphenyl solvent in water. Such one or more nonionic or amphoteric surfactants include those described below.

The concentrate compositions of the invention also include one or more nonionic surfactants. Practically any hydrophobic compound having a carboxy, hydroxy, amido, or amino group with a free hydrogen attached to the nitrogen can be condensed with ethylene oxide or with the polyhydration product thereof, polyethylene glycol, to form a water soluble nonionic surfactant compound. Further, the length of the polyethylenoxy hydrophobic and hydrophilic elements may various. Exemplary nonionic compounds include the polyoxyethylene ethers of alkyl aromatic hydroxy compounds, e.g., alkylated polyoxyethylene phenols, polyoxyethylene ethers of long chain aliphatic alcohols, the polyoxyethylene ethers of hydrophobic propylene oxide polymers, and the higher alkyl amine oxides.

To be mentioned as particularly useful nonionic surfactants are alkoxylated linear primary and secondary alcohols such as those commercially available under the tradenames PolyTergent® SL series (Olin Chemical Co., Stamford Conn.), Neodol® series (Shell Chemical Co., Houston Tex.), Genapol series (Clariant Corp., Charlotte, N.C.); as well as alkoxylated alkyl phenols including those commercially available under the tradename Triton® X series (Union Carbide Chem. Co., Danbury Conn.).

Further exemplary useful nonionic surfactants which may be used include alkanolamides including monoethanolamides and diethanolamides, particularly fatty monoalkanolamides and fatty dialkanolamides. Further exemplary nonionic surfactants which may be used include certain alkanolamides including monoethanolamides and diethanolamides, particularly fatty monoalkanolamides and fatty dialkanolamides. Commercially available monoethanol amides and diethanol amides include those marketed under the trade names Alakamide® and Cyclomide® by Rhône-Poulenc Co., (Cranbury, N.J.) and include Cyclomide® CDD-518 described to be a nonionic surfactant based on coconut diethanolamide; Cyclomide® C212 described to be a nonionic surfactant based on coconut monoethanolamide; Cyclomide® DC212 described to be a nonionic surfactant based on 2:1 coconut monoethanolamide; Cyclomide® DC212/M described to be a nonionic surfactant based on 2:1 modified coconut monoethanolamide; Cyclomide® DC212/S described to be a nonionic surfactant based on 1:1 coconut monoethanolamide; Cyclomide® DC212/SE described to be a nonionic surfactant based on 1:1 fatty acid diethanolamide; Cyclomide® DIN 100 described to be a nonionic surfactant based on lauric/linoleic diethanolamide; Cyclomide® DIN-295/S described to be a nonionic surfactant based on 1:1 linoleic diethanolamide; Cyclomide®

DL203 described to be a nonionic surfactant based on 2:1 lauric diethanolamide; Cyclomide® DL203/S described to be a nonionic surfactant based on 1:1 lauric diethanolamide; Cyclomide® DL207/S and Cyclomide® DL207/SL described to be nonionic surfactants based on 1:1 lauric/myristic diethanolamide; Cyclomide® DO280 described to be a nonionic surfactant based on 2:1 oleic diethanolamide; Cyclomide® DO280/S described to be a nonionic surfactant based on 1:1 oleic diethanolamide; Cyclomide® DS 280/S described to be a nonionic surfactant based on 1:1 stearic diethanolamide; Cyclomide® KD described to be a nonionic surfactant based on 1:1 coconut diethanolamide; Cyclomide® LE described to be a nonionic surfactant based on 1:1 lauric diethanolamide; Cyclomide® LIPA described to be a nonionic surfactant based on lauric monoisopropanolamide; Cyclomide® L203 described to be a nonionic surfactant based on lauric monoethanolamide; Cyclomide® S280 described to be a nonionic surfactant based on stearic monoethanolamide; Cyclomide® WRS 1–66 described to be a nonionic surfactant based on diethanolamides of unsaturated fatty acids; Cyclomide® 101 CG described to be an alkanolamide nonionic surfactant; Cyclomide® 200 CGN based on coconut oil diethanolamide; as well as Cyclomide® 206 CGN and Cyclomide® 210 CGN, both described to be a nonionic surfactants based on coconut alkanolamide.

Exemplary useful and commercially available monoethanol amides and diethanol amides include those marketed under the trade names Alakamide® and Cyclomide® by Rhône-Poulenc Co., (Cranbury, N.J.). Especially useful are lineolamide diethanolamides, such as MONAMID 15–70W (Mona Industries, Paterson N.J.).

Nonionic surfactant compositions based on amine oxides are useful in the inventive compositions.

One general class of useful amine oxides include alkyl di (lower alkyl) amine oxides in which the alkyl group has about 10–20, and preferably 12–16 carbon atoms, and can be straight or branched chain, saturated or unsaturated. The lower alkyl groups include between 1 and 7 carbon atoms. Examples include lauryl, dimethyl amine oxide, myristyl dimethyl amine oxide, and those in which the alkyl group is a mixture of different amine oxide, dimethyl cocoamine oxide, dimethyl (hydrogenated tallow) amine oxide, and myristyl/palmityl dimethyl amine oxide.

A further class of useful amine oxides include alkyl di (hydroxy lower alkyl) amine oxides in which the alkyl group has about 10–20, and preferably 12–16 carbon atoms, and can be straight or branched chain, saturated or unsaturated. Examples are bis(2-hydroxyethyl) cocoamine oxide, bis(2-hydroxyethyl) tallowamine oxide; and bis(2-hydroxyethyl) stearylamine oxide.

Further useful amine oxides include those which may be characterized as alkylamidopropyl di(lower alkyl) amine oxides in which the alkyl group has about 10–20, and preferably 12–16 carbon atoms, and can be straight or branched chain, saturated or unsaturated. Examples are cocoamidopropyl dimethyl amine oxide and tallowamidopropyl dimethyl amine oxide; and Additional useful amine oxides include those which may be referred to as alkylmorpholine oxides in which the alkyl group has about 10–20, and preferably 12–16 carbon atoms, and can be straight or branched chain, saturated or unsaturated.

A class of particularly useful nonionic surfactants are those based on alkoxylated, especially ethoxylated, glyceryl esters. Such compounds are known and commercially available. Examples of such materials include alkoxylated glyceryl cocoates, alkoxyalted glyceryl tallowates, may of which are available under the tradename VARONIC (Witco Chem. Co., Greenwich Conn.) Particularly useful is VARONIC LI-63 which is described to be an alkoxylated glyceryl cocoate which exhibits a hydrophilic/lipophilic balance ('HLB') value of about 15.9.

The inventive compositions may also include one or more amphoteric surfactants. Exemplary useful amphoteric surfactants include allylbetaines, particularly those which may be represented by the following structural formula:

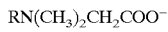

$RN(CH_3)_2CH_2COO^-$ wherein R is a straight or branched hydrocarbon chain which may include an aryl moiety, but is preferably a straight hydrocarbon chain containing from about 6 to 30 carbon atoms. Further exemplary useful amphoteric surfactants include amidoalkylbetaines, such as amidopropylbetaines which may be represented by the following structural formula:

$RCONHCH_2CH_2CH_2N^+(CH_3)_2CH_2COO^-$ wherein R is a straight or branched hydrocarbon chain which may include an aryl moiety, but is preferably a straight hydrocarbon chain containing from about 6 to 30 carbon atoms.

Particularly exemplary useful betaines include dodecyl dimethyl betaine, cetyl dimethyl betaine, dodecyl amidopropyldimethyl betaine, tetradecyldimethyl betaine, tetradecylamidopropyldimethyl betaine, and dodecyldimethylammonium hexanoate.

Water is added in order to provide 100% by weight of the concentrate composition. The water may be tap water, but is preferably distilled and/or deionized water. If the water is tap water, it is preferably appropriately filtered in order to remove any undesirable impurities such as organics or inorganics, especially minerals salts which are present in hard water which may thus interfere with the operation of the other constituents of the invention, as well as any other optional components of the liquid concentrates according to the invention.

Water is added in amounts which are sufficient to form the concentrated compositions which amount is sufficient to ensure the retention of a substantially clear characteristic when produced as a concentrate, but at the same time ensuring good blooming upon the addition of the concentrated composition to a further amount of water, or upon the addition of further water to the concentrate.

Other conventional additives known to the art but not expressly enumerated here may also be included in the compositions according to the invention. By way of non-limiting example without limitation these may include : chelating agents, coloring agents, light stabilizers, fragrances, thickening agents, hydrotropes, pH adjusting agents, and pH buffers. Many of these materials are known to the art, per se, and are described in *McCutcheon's Detergents and Emulsifiers*, North American Edition, 1982; *Kirk-Othmer, Encyclopedia of Chemical Technology*, 3rd Ed., Vol. 22, pp. 346–387, the contents of which are herein incorporated by reference. Such optional, i.e., non-essential constituents should be selected so to have little or no detrimental effect upon the desirable characteristics of the present invention, namely the blooming behavior, cleaning efficacy, disinfectant activity, and low toxicity as provided by the inventive compositions. Generally the total weight of such further conventional additives may comprise up to 20% by weight of a concentrated composition formulation.

One optional but frequently desirable constituent which is included in the inventive compositions is an acid constituent, which may be an inorganic acid such as hydrochloric acid but is preferably a water soluble organic acid such as citric acid. When included in the compositions, the acid constituent provides a useful pH buffering effect.

Further optional, but advantageously included constituents are one or more coloring agents which find use in modifying the appearance of the concentrate compositions and enhance their appearance from the perspective of a consumer or other end user. Known coloring agents, may be incorporated in the compositions in effective amount to improve or impart to concentrate compositions an appearance characteristic of a pine oil type concentrate composition, such as a color ranging from colorless to a deep amber, deep amber yellow or deep amber reddish color. Such a coloring agent or coloring agents may be added in any useful amount in a conventional fashion, i.e., admixing to a concentrate composition or blending with other constituents used to form a concentrate composition. However, other colors atypical of pine oil type cleaning concentrates may be used as well. Known art light stabilizer constituents useful in pine oil type compositions may also be added, particularly wherein coloring agents are used in a composition. As is known to the art, such light stabilizers act to retain the appearance characteristics of the concentrate compositions over longer intervals of time.

Exemplary useful buffers include the alkali metal phosphates, polyphospates, pyrophosphates, triphosphates, tetraphosphates, silicates, metasilicates, polysilicates, carbonates, hydroxides, and mixtures of the same. Certain salts, such as the alkaline earth phosphates, carbonates, hydroxides, can also function as buffers. It may also be suitable to use buffers such materials as aluminosilicates (zeolites), borates, aluminates and certain organic materials such as gluconates, succinates, maleates, and their alkali metal salts. Such buffers keep the pH ranges of the compositions of the present invention within acceptable limits.

Exemplary useful pH adjusting agents include known materials such as organic acids or inorganic acids, as well as alkaline materials, which may be used to adjust the pH of the concentrate compositions to a desired range.

One optional constituent which is desirably included is one or more chelating agents. Useful as chelating agents include those known to the art, inter alia: gluconic acid, tartartic acid, citric acid, oxalic acid, lactic acid, nitrilotriacetic acid, polyacrylic acid salts, diethylene triamine pentaacetic acid, and their water soluble salts, especially the alkali metal salts and particularly the sodium salts thereof, as well as aminopolycarboxylic acids and salts thereof wherein the amino nitrogen has attached thereto two or more substituent groups, including sodium and potassium salts of ethylenediaminetetraacetic acid, diethylenetriaminepentaacetic acid, N-hydroxyethylethylenediaminetriacetic acid. It has been observed that sodium or potassium salts of an ethylenediaminetetraacetic acid, most preferably mono-, di- or tri-alkali or alkaline salts of of ethylenediaminetetraacetic acid is very advantageously included in the inventive concentrate compositions particularly wherein d-limonene is present and especially where d-Limonene is the sole terpene solvent containing constituent.

What is to be understood by the term "concentrate" and "concentrate composition" in this specification and claims is the pre-consumer dilution and composition of the cleaning composition which is the essentially the form of the product prepared for sale to the consumer or other end user. Such a consumer or other end user would then normally be expected to dilute the same with water to form a cleaning composition. It is to be understood however that nothing in this invention would bar its use as cleaning composition without any further dilution and it may be used in the concentrations in which it was prepared for sale. Similarly, what is to be understood by the term "cleaning compositions" are the water diluted compositions which are expected to be prepared by the consumer or other end user by mixing a measured amount of the "concentrate" with water in order to form an appropriately diluted cleaning composition which is suitable for use in cleaning applications, especially in the cleaning of hard surfaces.

It is also to be understood, that proportions of one or more constituents have been and generally are referred to as percent by weight or as parts by weight based on a measure of 100% by weight, unless otherwise indicated.

According to certain particularly preferred embodiments of the invention there are provided aqueous concentrated liquid disinfectant composition which comprise the following constituents:

1–12% wt. terpene solvent containing constituent;
1–5% wt. germicidal cationic surfactant, preferably a quaternary ammonium compound having germicidal properties;
0.1–15% wt. organic solvent constituent;
1–12% wt. binary co-solvent system comprising alkyl biphenyl solvent and a co-solvent;
1–20% wt. one or more nonionic surfactants;
optionally to 20% wt. of at least one optional constituent selected from: chelating agents, coloring agent, light stabilizers, fragrances, thickening agents, hydrotropes, pH adjusting agents, pH buffers one or more detersive surfactant constituents particularly non-ionic and amphoteric surfactants, as well as others known the art,
and, to 100% wt. of water.

As generally denoted above, the formulations according to the invention include both cleaning compositions and concentrates as outlined above which differ only in the relative proportion of water to that of the other constituents forming such formulations. While the concentrated form of the cleaning compositions find use in their original form, they are more frequently used in the formation of a cleaning composition therefrom. Such may be easily prepared by diluting measured amounts of the concentrate compositions in water by the consumer or other end user in certain weight ratios of concentrate:water, and optionally, agitating the same to ensure even distribution of the concentrate in the water. As noted, the concentrate may be used without dilution, i.e., in concentrate:water concentrations of 1:0, to extremely dilute dilutions such as 1:10,000. Desirably, the concentrate is diluted in the range of 1:0.1–1:1000, preferably in the range of 1:1–1:500 but most preferably in the range of 1:10–1:100. The actual dilution selected is in part determinable by the degree and amount of dirt and grime to be removed from a surface(s), the amount of mechanical force imparted to remove the same, as well as the observed efficacy of a particular dilution. Generally better results and faster removal is to be expected at lower relative dilutions of the concentrate in water.

In accordance with preferred embodiments of the invention, when a quantity of the concentrate compositions taught herein are added to a larger volume of water, a blooming characteristic is manifested. Such "blooming" may be broadly characterized as the formation of milky, creamy or cloudy appearance which is manifested when a dilutable composition is added to a larger volume or quantity of water. Such "blooming" may be alternately characterized as the reduction of transmitted light through an amount of water by at least 30%, desirably by at least 40%, yet more desirably by at least about 50%, and yet most desirably by at least 60% or more when a dilution of the concentrate composition:water with the weight or volume ratio range of from 1:64–102 is formed. That such blooming may be attained without the use of pine oil fractions as is common in certain commercially available pine oil containing preparations is surprising.

As has been noted, concentrate compositions according to preferred embodiments of the invention exhibit both a substantive blooming effect and a long lasting blooming effect when they are diluted into a larger volume of water, especially when used to form (weight ratio) dilutions with water of concentrate:water of 1:64 at room temperature. Desirably, such dilutions do not exhibit an increase in light transmittance in accordance with the measurement methods discussed in the Examples below, of more than 50% (based on the initial 'as mixed' value) during its initial three-day interval, and especially during its initial seven-day interval.

The concentrate compositions according to the invention, and aqueous dilutions formed therefrom, are particularly useful in the sanitization of hard surfaces. By way of non-limiting example, hard surfaces include surfaces composed of refractory materials such as: glazed and unglazed tile, brick, porcelain, ceramics as well as stone including marble, granite, and other stones surfaces; glass; metals; plastics e.g. polyester, vinyl; fiberglass, Formica®, Corian® and other hard surfaces known to the art. Hard surfaces which are to be particularly denoted include those associated with kitchen environments, lavatory environments, especially flooring surfaces and the surfaces of fixtures (doors, cabinets, shelving, and the like) in such environments.

The compositions according to the invention exhibit sanitizing properties, and are useful in the sanitization of surfaces wherein the presence of various viruses, molds, fungi, bacteria, and mildew are suspected.

In preferred embodiments, aqueous dilutions of the concentrated aqueous liquid disinfectant compositions exhibit antimicrobial efficacy against at least one of the following bacteria: *Staphylococcus aureus, Salmonella choleraesuis, Pseudomonas aeruginosa,* where the ratio of concentrate composition:water is 1:64 to 1:102. According to more preferred embodiments, aqueous dilutions of the concentrated aqueous liquid disinfectant compositions exhibit antimicrobial efficacy against at least two of the following bacteria: *Staphylococcus aureus, Salmonella choleraesuis, Pseudomonas aeruginosa,* where the ratio of concentrate composition:water of 1:64 to 1:102. Such aqueous dilutions may be classified as "broad spectrum disinfectant" compositions. According to a still more preferred embodiment, aqueous dilutions of the concentrated aqueous liquid disinfectant compositions exhibit antimicrobial efficacy against all three of the following bacteria: *Staphylococcus aureus, Salmonella choleraesuis, Pseudomonas aeruginosa,* where the ratio of concentrate composition:water of 1:64 to 1:102. Such aqueous dilutions may be classified as "hospital strength disinfectant" compositions. In each of these respective preferred, more preferred and still more preferred embodiments described immediately above, those which exhibit antimicrobial efficacy at greater aqueous dilutions of the concentrated aqueous liquid disinfectant compositions in water, such as at concentrate:water dilution ratios ratios of 1:102, are preferred over concentrate:water dilution ratios of 1:85, and still more preferred over concentrate:water dilution ratios of 1:64.

Such dilution ratios of concentrate:water as described above may be volume/volume basis, or a weight/weight basis.

The following examples below illustrate exemplary and among them preferred formulations of the composition according to the instant invention. It is to be understood that these examples are presented by means of illustration only and that further useful formulations fall within the scope of this invention and the claims may be readily produced by one skilled in the art and not deviate from the scope and spirit of the invention.

EXAMPLES

A number of formulations were produced by mixing the constituents outlined in Table 1 by adding the individual constituents into a beaker of deionized water at room temperature which was stirred with a conventional magnetic stirring rod. The order of addition is not critical, but good results are obtained where the surfactants are added to the water prior to Stirring continued until the formulation was homogenous in appearance. It is to be noted that the constituents might be added in any order, but it is preferred that water be the initial constituent provided to a mixing vessel or apparatus as it is the major constituent and addition of the further constituents thereto is convenient. The exact compositions of the example formulations are listed on Table 1, below. Attention is directed to the fact that the formulations in Table 1 were substantially the same, except for the amounts of terpene containing solvent and biphenyl solvent which were included in the formulations.

TABLE 1

| | Notebook Ref: | | | | | | |
|---|---|---|---|---|---|---|---|
| | 517-098D Comp. 1 | 517-098A Ex. 1 | 517-098B Ex. 2 | 517-098C Ex. 3 | 546-084A Ex. 4 | 546-084B Ex. 5 | 546-086 Ex. 6 |
| Pine Oil 60 | 9.00 | 3.00 | 6.00 | 8.00 | 5.00 | 4.00 | 7.00 |
| Isopropyl alcohol | 12.00 | 12.00 | 12.00 | 12.00 | 12.00 | 12.00 | 12.00 |
| Genapol ® 26-L-80 | 6.00 | 6.00 | 6.00 | 6.00 | 6.00 | 6.00 | 6.00 |
| Varonic LI-63 | 1.70 | 1.70 | 1.70 | 1.70 | 1.70 | 1.70 | 1.70 |
| Ammonyx CDO Special | 0.75 | 0.75 | 0.75 | 0.75 | 0.75 | 0.75 | 0.75 |
| Monamid 15-70W | 2.00 | 2.00 | 2.00 | 2.00 | 2.00 | 2.00 | 2.00 |
| BTC-835 | 1.60 | 1.60 | 1.60 | 1.60 | 1.60 | 1.60 | 1.60 |
| BTC-818 | 1.00 | 1.00 | 1.00 | 1.00 | 1.00 | 1.00 | 1.00 |
| benzyl alcohol | 0.75 | 0.75 | 0.75 | 0.75 | 0.75 | 0.75 | 0.75 |
| biphenyl solvent | 0.00 | 6.00 | 3.00 | 1.00 | 4.00 | 5.00 | 2.00 |
| citric acid | 0.05 | 0.05 | 0.05 | 0.05 | 0.05 | 0.05 | 0.05 |
| di water | q.s. | q.s. | q.s. | q.s. | q.s. | q.s. | q.s. |

| | Notebook Ref: | | | | |
|---|---|---|---|---|---|
| | 546-107A Ex. 7 | 546-107B Ex. 8 | 546-107C Ex. 9 | 546-107E Ex. 10 | 546-109A Ex. 11 |
| d-Limonene | 4.00 | 4.00 | 3.00 | 5.00 | 6.00 |
| Isopropyl alcohol | 12.00 | 12.00 | 12.00 | 12.00 | 12.00 |
| Genapol ® 26-L-80 | 6.00 | 6.00 | 6.00 | 6.00 | 6.00 |
| Varonic LI-63 | 1.70 | 1.70 | 1.70 | 1.70 | 1.70 |
| Ammonyx CDO Special | 0.75 | 0.75 | 0.75 | 0.75 | 0.75 |
| Monamid 15-70W | 2.00 | 2.00 | 2.00 | 2.00 | 2.00 |
| BTC-835 | 1.60 | 1.60 | 1.60 | 1.60 | 1.60 |
| BTC-818 | 1.00 | 1.00 | 1.00 | 1.00 | 1.00 |
| benzyl alcohol | 0.75 | 0.75 | 0.75 | 0.75 | 0.75 |
| biphenyl solvent | 3.50 | 3.00 | 4.00 | 2.00 | 1.00 |
| Na$_2$EDTA | 1.00 | 1.50 | 1.50 | 1.50 | 1.50 |
| citric acid | 0.05 | 0.05 | 0.05 | 0.05 | 0.05 |
| di water | q.s. | q.s. | q.s. | q.s. | q.s. |

The specific identity of the constituents of Table 1 are indicated on Table 2, below. All of the formulations on Table 1 indicated in weight percent, and the percent actives of individual constituents are 100% unless otherwise indicated.

TABLE 2

| | |
|---|---|
| Pine Oil 60 | pine oil preparation containing at least 60% alpha terpinol |
| d-limonene | monoterpene containing at least 90% wt. of d-limonene |
| Isopropyl alcohol | propan-2-ol |
| Genapol ® 26-L-80 | Linear C12–C16 alcohol ethoxylate, average of 9 moles of ethylene oxide |
| Varonic ® LI-63 | PEG 30 glyceryl cocoate nonionic surfactant |
| Ammonyx ® CDO Special | cocoamidopropyldimethylamine oxide |
| Monamid ® 15–70W | lineolamide diethanolamine |
| BTC-835 | n-alkyl dimethyl benzyl ammonium chloride |
| BTC-818 | dialkyl dimethyl ammonium chloride |
| benzyl alcohol | phenylmethanol |
| biphenyl solvent | NUSOLV ABP-103, diisopropylbiphenyl solvent |
| Na2EDTA | disodium salt of ethylene diamine tetraacetic acid |
| citric acid | citric acid, anhydrous |
| di water | deionized water |

The blooming characteristics of these formulations was characterized by using the Brinkman Sybron PC 801 calorimeter. Each tested formulation were diluted with deionised water in a weight ratio of 1:64, and the test was carried out with each of the formulations and water at room temperature (68° F., 20° C.). The resulting determined values, reported as "blooming" in the following table provide an empirical evaluation in percent transmittance (%) of the degree of transparency of a diluted example formulation wherein 0% indicates complete opacity and 100% the transparency of a deionised water sample. The results are reported as follows:

TABLE 3

| | Initial | 1 hour | 2 hours | 4 hours | 6 hours | 24 hours | 48 hours | 72 hours | 96 hours | 168 hours |
|---|---|---|---|---|---|---|---|---|---|---|
| Comp. 2 | 70.7 | 75.1 | 75.7 | 76.3 | 76.9 | 81.4 | 83.3 | 86.7 | 89.4 | 93.7 |
| Ex. 1 | 98.7 | 93.5 | 87.0 | 76.0 | 68.5 | 26.0 | 10.8 | 5.3 | 3.2 | 1.3 |
| Ex. 2 | 99.8 | 99.8 | 99.7 | 99.4 | 99.9 | 100 | 99.1 | 99.4 | 99.2 | 99.8 |
| Ex. 3 | 67.3 | 76.3 | 77.4 | 78.4 | 79.0 | 82.7 | 82.4 | 84.7 | 85.7 | 88.6 |
| Ex. 4 | 99.9 | 98.8 | 96.7 | 93.4 | 91.8 | 75.4 | 66.6 | 59.6 | 56.6 | 52.4 |
| Ex. 5 | 99.3 | 96.2 | 92.3 | 85.4 | 81.6 | 47.8 | 29.3 | 19.8 | 14.9 | 8.4 |
| Ex. 6 | 83.4 | 90.5 | 91.3 | 92.0 | 92.3 | 95.6 | 94.5 | 95.6 | 96.0 | 96.6 |
| Ex. 7 | 98.1 | 89.9 | 78.0 | 73.5 | — | 31.5 | 21.1 | 19.4 | — | 23.2 |
| Ex. 8 | 98.6 | 91.3 | 85.0 | 76.0 | — | 39.5 | 40.6 | 53.0 | — | 78.8 |
| Ex. 9 | 98.3 | 90.4 | 83.7 | 73.9 | — | 27.4 | 14.7 | 11.3 | — | 8.9 |
| Ex. 10 | 98.1 | 90.1 | 82.2 | 71.9 | — | 50.3 | 79.7 | 92.5 | — | 100 |
| Ex. 11 | 99.5 | 100 | 99.6 | 100 | — | 100 | 100 | 100 | — | 100 |

Comparative 2 (Comp. 2) was a 1:64 aqueous dilution of a composition identical to Ex. 3, but which included 0% biphenyl solvent, and 9% wt. of the pine oil constituent
'—' indicates that the light transmittance was not tested for the indicated time interval As may be seen from the results indicated on Table 3, the formulation according to comparative example 2 (Comp.2) which did not include the biphenyl solvent provided good blooming properties. Dilutions formed from concentrate compositions according to the invention (Ex.1, Ex.4, Ex.5, Ex.7 and Ex.9) each of which included the biphenyl solvent but which had reduced amounts of pine oil constituents the concentrate compositions according to Ex.1, Ex.4, Ex.5, Ex.7 and Ex.9 provided better blooming than the formulation of Comp.2 This was particularly evident in the latter days of the test.

Evaluation of Antimicrobial Efficacy

Several of the exemplary formulations described in more detail on Table 1 above were evaluated in order to evaluate their antimicrobial efficacy against *Staphylococcus aureus* (gram positive type pathogenic bacteria) (ATCC 6538), *Salmonella choleraesuis* (gram negative type pathogenic bacteria) (ATCC 10708), and *Pseudomonas aeruginosa* (gram negative type pathogenic bacteria) (ATCC 15442). The testing was performed in accordance with the protocols outlined in "Use-Dilution Method", Protocols 955.14, 955.15 and 964.02 described in Chapter 6 of "Official Methods of Analysis", 16$^{th}$ Edition, of the Association of Official Analytical Chemists; "Germicidal and Detergent Sanitizing Action of Disinfectants", 960.09 described in Chapter 6 of "Official Methods of Analysis", 15th Edition, of the Association of Official Analytical Chemists; or American Society for Testing and Materials (ASTM) E 1054-91 the contents of which are herein incorporated by reference. This test is also commonly referred to as the "AOAC Use-Dilution Test Method".

As is appreciated by the skilled practitioner in the art, the results of the AOAC Use-Dilution Test Method indicates the number of test substrates wherein the tested organism remains viable after contact for 10 minutes with at test disinfecting composition/total number of tested substrates (cylinders) evaluated in accordance with the AOAC Use-Dilution Test. Thus, a result of "0/60" indicates that of 60 test substrates bearing the test organism and contacted for 10 minutes in a test disinfecting composition, 0 or 1 test substrates had viable (live) test organisms at the conclusion of the test. Such a result is excellent, illustrating the excellent disinfecting efficacy of the tested composition.

Results of the antimicrobial testing are indicated on the Table, below. The reported results indicate the number of test cylinders with live test organisms/number of test cylinders tested for each example formulation and organism tested.

TABLE

| | Antimicrobial Efficacy | |
|---|---|---|
| Formulation | *Staphylococcus aureus* | *Salmonella choleraesuis* |
| Ex. 1 | 0/60 | 0/60 |
| Ex. 2 | 0/60 | 0/60 |
| Ex. 3 | 1/60 | 0/60 |

As may be seen from the results indicated above, the compositions according to the invention provide excellent sanitizing benefits to hard surfaces as demonstrated by the excellent antimicrobial efficacy of these compositions against known bacteria commonly found in bathroom, kitchen and other environments. Such advantages clearly illustrate the superior characteristics of the compositions, the cleaning and antimicrobial benefits attending its use which is not before known to the art.

Cleaning Test

Cleaning efficacy was measured for weight ratios of 1:64 (concentrate composition:water) aqeuous dilutions of formulations according to each of Ex. 1, 2 and 3 and as a control, a similar aqueous dilution of the formulation according to Comp. 1 described above. The test was carried out using the ASTM D4488-89, Annex A2 method—greasy soil on painted masonite wallboard test, using a Gardner Washability Apparatus.

Latex painted masonite wallboard is soiled with a mixture of melted, oily soils containing a small amount of carbon black and allowed to set overnight. A first aqueous dilution is applied to a sponge that scrubs half the soiled substrate in a straight-line using the Gardner Washability Apparatus. Afterwards, the second aqueous dilution is applied to a further sponge that scrubs the other half of the soiled substrate in a similar manner.

In determining the cleaning efficiency, reflectance values were determined using a Gardner Lab Scan Reflectometer for each of the following: a clean unsoiled panel, a soiled panel, and a soiled panel following Gardner Washability Apparatus scrubbing. Such reflectance values were then employed to calculate % cleaning efficiency according to the following formula:

$$\% \text{ Cleaning Efficiency} = \frac{Lt - Ls}{Lo - Ls} \times 100\%$$

wherein,
Lt=% reflectance average after scrubbing solid tile
Ls=% reflectance average before cleaning soiled tile
Lo=% reflectance average original tile before soiling
Cleaning efficiency results for Formulation 1 are shown on Table 4.

TABLE 4

| Formulation:water (1:64) w/w dilution | Lo | Ls | Lt | % Cleaning Efficiency |
|---|---|---|---|---|
| Comp. 1 | 93.48 | 26.70 | 67.84 | 61.60 |
| Ex. 1 | 93.58 | 27.73 | 66.89 | 59.47 |
| Ex. 2 | 93.19 | 25.44 | 66.34 | 60.37 |
| Ex. 3 | 93.70 | 27.20 | 67.06 | 59.94 |

As numerical values for a % Cleaning Efficiency increase, higher cleaning effectiveness is achieved for the cleaning composition tested. As the results show, the inventive composition showed an excellent cleaning property.

What is claimed is:

1. An aqueous concentrated liquid disinfectant composition which blooms when added to a larger volume of water which comprises the following constituents:

a terpene based solvent;

as a germicidal cationic surfactant, a quaternary ammonium compound having germicidal properties;

a further organic solvent constituent;

a binary co-solvent system comprising alkyl biphenyl solvent and a co-solvent which aids in the solubilization of the alkyl biphenyl solvent in water;

one or more nonionic surfactants;

optionally at least one optional constituent selected from: chelating agents, coloring agent, light stabilizers, fragrances, thickening agents, hydrotropes, pH adjusting agents, pH buffers one or more detersive surfactant constituents; and, the balance being water.

2. The aqueous concentrated liquid disinfectant composition according to claim 1 wherein the terpene based solvent constituent is solely a d-limonene constituent.

3. The aqueous concentrated liquid disinfectant composition according to claim 1 wherein the terpene based solvent constituent is solely a pine oil constituent.

4. The aqueous concentrated liquid disinfectant composition according to claim 1 wherein the quaternary ammonium compound having germicidal properties is represented by the formula:

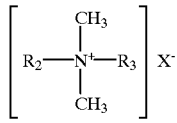

wherein $R_2$ and $R_3$ are the same or different $C_8$–$C_{12}$ alkyl groups, or $R_2$ is $C_{12-16}$ alkyl, $C_{8-18}$ alkylethoxy, $C_{8-18}$ alkylphenolethoxy when $R_3$ is benzyl, and X is a halide.

5. The aqueous concentrated liquid disinfectant composition according to claim 1 wherein the alkyl biphenyl solvent is represented according to the structure:

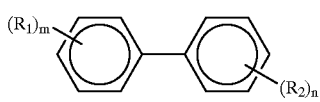

wherein:

$R_1$ is hydrogen or is a lower alkyl radical, $R_2$ is a $C_1$–$C_{10}$ which may be straight chained or branched alkyl radical, m is an integer from 1–3 inclusive; and, n is an integer from 1–3 inclusive.

6. The aqueous concentrated liquid disinfectant composition according to claim 5 wherein:

$R_1$ is hydrogen, m is 1, n is an integer from 1–3 inclusive, and, $R_2$ is a $C_1$–$C_6$ straight chained or branched alkyl radical.

7. The aqueous concentrated liquid disinfectant composition according to claim 1 wherein the terpene based solvent constituent is present with respect to the alkyl biphenyl solvent in a respective weight ratio of from 8:1 to 1:2, with the total amount of these combined constituents not exceeding 9% by weight of the total weight of the concentrate compositions.

8. The aqueous concentrated liquid disinfectant composition according to claim 1 wherein the alkyl biphenyl solvent is present in a respective weight ratio of d-limonene constituent:alkyl biphenyl solvent of from 4:3.5 to 5:2.

9. The aqueous concentrated liquid disinfectant composition according to claim 1 wherein the alkyl biphenyl solvent is present in a respective weight ratio of pine oil constituent: alkyl biphenyl solvent of from 8:1 to 3:6.

10. A process for disinfecting a hard surface where the presence of gram positive or gram negative bacteria is suspected which comprises the process step of:

contacting the hard surface with a disinfecting effective amount of the aqueous concentrated liquid disinfectant composition according to claim 1.

11. The aqueous concentrated liquid disinfectant composition according to claim 5 wherein the alkyl biphenyl solvent is represented by the structure:

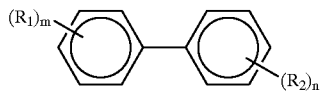

wherein:

$R_1$ is hydrogen or a $C_1$–$C_6$ straight chained or branched alkyl radical, $R_2$ is a $C_1$–$C_6$ straight chained or branched alkyl radical, m is an integer from 1–3 inclusive; and, n is an integer from 1–3 inclusive.

12. The aqueous concentrated liquid disinfectant composition according to claim 5 which further comprises one or more additional detersive surfactant constituents selected from non-ionic and amphoteric detersive surfactants.

* * * * *